(12) United States Patent
McCafferty et al.

(10) Patent No.: US 9,226,802 B2
(45) Date of Patent: Jan. 5, 2016

(54) POLYMERIC INSTRUMENT FOR CLEANING CANALS IN ENDODONTIC PROCEDURES

(76) Inventors: Ryan J. McCafferty, Wall, NJ (US); Michael Quigley, Toms River, NJ (US)

(*) Notice: Subject to any disclaimer, the term of this patent is extended or adjusted under 35 U.S.C. 154(b) by 168 days.

(21) Appl. No.: 13/342,149

(22) Filed: Jan. 2, 2012

(65) Prior Publication Data

US 2013/0171581 A1 Jul. 4, 2013

(51) Int. Cl.
*A61C 5/02* (2006.01)
*A61C 19/04* (2006.01)

(52) U.S. Cl.
CPC ............ *A61C 5/023* (2013.01); *A61C 5/025* (2013.01); *A61C 19/041* (2013.01)

(58) Field of Classification Search
CPC ....... A61C 5/023; A61C 5/025; A61C 19/041
USPC .............................. 433/81, 102, 141, 164, 224
See application file for complete search history.

(56) References Cited

U.S. PATENT DOCUMENTS

| | | | |
|---|---|---|---|
| 717,594 A | 1/1903 | Miles, Jr. | |
| 4,280,518 A | 7/1981 | Gambaro | |
| 4,832,061 A | 5/1989 | Hwang | |
| 5,775,346 A | 7/1998 | Szyszkowski | |
| 5,899,693 A | 5/1999 | Himeno et al. | |
| 6,012,921 A * | 1/2000 | Riitano | 433/102 |
| 6,059,570 A | 5/2000 | Dragan et al. | |
| 6,082,999 A | 7/2000 | Tcherny et al. | |
| 6,085,761 A | 7/2000 | Inaba | |
| 6,179,617 B1 | 1/2001 | Ruddle | |
| D441,141 S | 4/2001 | Shalita | |
| 6,293,794 B1 * | 9/2001 | McSpadden | 433/102 |
| 6,343,929 B1 | 2/2002 | Fischer | |
| 6,347,941 B1 * | 2/2002 | Boston | 433/165 |
| 6,428,317 B1 * | 8/2002 | Abel | 433/102 |
| 6,491,520 B1 | 12/2002 | Carlsson et al. | |
| 6,634,051 B1 | 10/2003 | Dragan et al. | |
| 6,638,067 B2 | 10/2003 | Fischer et al. | |
| 6,981,869 B2 | 1/2006 | Ruddle | |
| 7,677,296 B2 * | 3/2010 | Mason | 164/122 |
| 2002/0172922 A1 * | 11/2002 | Mannschedel | 433/102 |
| 2003/0211442 A1 * | 11/2003 | Abel | 433/102 |
| 2004/0031114 A1 * | 2/2004 | Dragan et al. | 15/106 |
| 2004/0121283 A1 * | 6/2004 | Mason | 433/102 |
| 2005/0136375 A1 * | 6/2005 | Sicurelli et al. | 433/81 |
| 2006/0068362 A1 * | 3/2006 | Desrosiers et al. | 433/102 |

OTHER PUBLICATIONS

Dupont.com. DuPont Engineering Polymers, Copyright 2008 [retrieved on Feb. 11 2013]. Retrieved from the Internet: http://plastics.dupont.com/plastics/pdflit/americas/markets/Tech_Healthcare_1 1_2009.pdf.*
Daniel M. Keir, "Effectiveness of a Brush in Removing Postinstrumentation Canal Debris," Journal of Endodontics, vol. 16, No. 7, Jul. 1990, pp. 323-327.
Cohen & Burns, Pathways to the Pulp, 8th ed. (2002), pp. xiii, 261-262.

* cited by examiner

*Primary Examiner* — Heidi M Eide
(74) *Attorney, Agent, or Firm* — Ice Miller LLP

(57) ABSTRACT

An instrument for cleaning canals during endodontic procedures is presented. The instrument is formed in one piece from a stiff polymeric material. The instrument features a handle, a measuring shaft, and a tapering shank with raised polymeric projections along its length. The present invention is designed without the use of bristles that conventional brushes contain. The raised polymeric projections include fins that may be oriented parallel to or transverse to the axis of the instrument to provide multidirectional cleaning capability. The instrument is stiff enough to penetrate a canal and mechanically scrub and scrape canal surfaces, but flexible enough to negotiate the curves of the canal.

19 Claims, 2 Drawing Sheets

POLYMERIC INSTRUMENT FOR CLEANING CANALS IN ENDODONTIC PROCEDURES

BACKGROUND

Endodontic therapy is a sequence of treatment for the pulp of a tooth which results in the elimination of infection and protection of the decontaminated tooth from future microbial invasion. This set of procedures is commonly referred to as a "root canal." Root canals and their associated pulp chamber are the physical hollows within a tooth that are naturally inhabited by nerve tissue, blood vessels and other cellular entities. Endodontic therapy involves the removal of these structures, the subsequent cleaning, shaping, and decontamination of the hollows with tiny files and irrigating solutions, and the obturation (filling) of the decontaminated canals with an inert filling such as gutta percha and typically a eugenol-based cement. After endodontic surgery the tooth will be "dead," and if an infection is spread at apex, root end surgery is required.

In the situation that a tooth is considered so threatened (because of decay, cracking, etc.) that future infection is considered likely or inevitable, a pulpectomy, removal of the pulp tissue, is advisable to prevent such infection. Usually, some inflammation and/or infection is already present within or below the tooth. To cure the infection and save the tooth, the dentist drills into the pulp chamber and removes the infected pulp and then drills the nerve out of the root canal(s) with long needle-shaped drills. The dentist then cleans and shapes (debrides) the canal using a file. The canal is then irrigated thoroughly, using a bleach solution. After this is done, the dentist fills each of the root canals and the chamber with an inert material, typically gutta percha, and seals up the opening. With the removal of nerves and blood supply from the tooth, it is best that the tooth be fitted with a crown which improves the prognosis of the tooth.

A successful procedure (one that does not require retreatment) depends in large part on how thoroughly the canals are debrided and irrigated prior to filling. During canal preparation, the file debrides the canal of larger materials, and the sodium hypochlorite solution helps digest and remove pulp and bacteria, viruses, spores, endotoxins and other irritants generated by the microorganisms in the canal system. However, studies have shown that even the most thorough use of sodium hypochlorite does not remove all the material from the root canals. The walls of a root canal are comprised of dentin which contains millions of dentinal tubules per square millimeter, and the irritants can find their way into the tubules of the root canal systems. Thus, after cleaning and shaping procedures, the root canal is still covered with a film of debris, frequently described in the literature as a "smear layer." This "smear layer" includes dentinal mud and/or organic debris. This smear layer is generally not removed by the action of a file, because the file does not have the requisite flexibility in terms of its shape, to thoroughly clean the walls of the canal, and remove the smear layer from the walls. In addition, endodontic files are usually round along the length, while pulp canals are ovoid. Because of this, many areas of the canal are mechanically untouched by the file. The "smear layer" can include microorganisms that may reinfect the tooth, thereby requiring retreatment.

SUMMARY

The present invention is an instrument for cleaning a canal of a tooth after debriding of the canal with a file, having a handle and a shank collinear with the handle, wherein the shank tapers over a length from a proximal end to a tip at a distal end of the shank, and wherein the shank is entirely composed of a polymeric composition and the shank is sized so that the distal end can reach an apical third of the canal, and a plurality of raised projections on the shank for a portion of the length of the shank that reaches the apical third, wherein the raised projections are composed of the same polymeric composition as the shank, and wherein the handle, shank and raised projections are formed in one piece. The present invention is uniquely designed without the use of bristles that conventional brushes contain, and instead utilizes fins and raised projections to provide a scrubbing and scrapping cleaning action.

The raised projections include raised bumps on the surface of the shank, and fins that vary in orientation between parallel with an axis of the shank, and transverse to the axis of the shank. The raised projections may be spaced more densely near the distal end than at the proximal end of the shank.

The instrument may further include a shaft collinear with the shank, having a series of markings indicating the depth to which the instrument has been inserted in the canal.

The instrument may be composed of a stiff polymeric material, having a flexural modulus between 2500 and 3500 MPa. Specifically, the instrument may be composed entirely of a medium density acetal polymeric material.

BRIEF DESCRIPTION OF THE DRAWINGS

The invention can be better understood with reference to the following drawings and description. The components in the figures are not necessarily to scale, emphasis instead being placed upon illustrating the principles of the invention. In the drawings.

DETAILED DESCRIPTION

Figure 1:
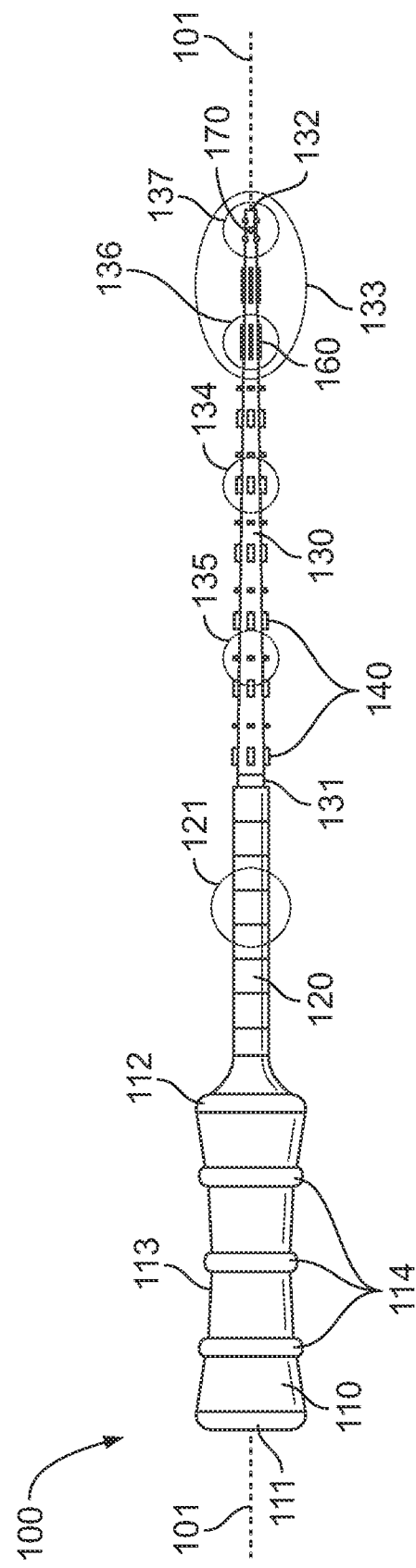
FIG. 1 is a lengthwise schematic view of an embodiment of the instrument according to the present invention.

As shown in FIG. 1, an instrument 100 according to the present invention includes a handle 110, a measuring shaft 120, and shank 130, all of which are coaxial around axis 101. The overall length of the instrument 100 is ranges from 26 to 46 mm, with 36 mm being preferred for most applications. The shank 130 has stiff raised polymeric projections 140 that extend radially outward from shank 130. The handle 110, shaft 120, shank 130 and raised projections 140 are formed in a unitary molding process using a polymeric material.

The polymeric material is any polymeric material that has sufficient stiffness to be driven into the deepest portions of the debrided root canal, yet has sufficient flexibility to negotiate the curvature of the canals, and to be rotated inside the canal for cleaning. The same material should be sufficiently stiff so that the raised projections 140 can effectively scrub the walls of the canal, but have sufficient flexibility to allow them to enter tight spaces in the canal, ideally having a flexural modulus between 2500 and 3500 MPa. The polymeric material must also be FDA approved for use in medical devices. A preferred polymeric material is a medium viscosity acetal homopolymer sold by DuPont under the name Delrin SC655. This material has a flexural modulus of approximately 2900 MPa.

The handle 110 is a polymeric cylinder, ranging from 8 mm to 12 mm in length, having sufficient length to be gripped between the thumb and forefinger of a dental practitioner. The handle is ideally wider at the ends 111 and 112 of the length of the handle 110, and narrower in the middle 113. This assists the grip between the thumb and forefinger of the dental practitioner, such that the practitioner can easily rotate the handle 110, and thus the instrument 100, around axis 101 in order to agitate the instrument 100 inside a canal. To achieve this purpose, the handle 110 ranges from 1.5 mm to 6 mm in diameter with the diameter greater at the ends 111 and 112 tapering to a smaller diameter in the middle portion 113. In order to further improve the grip, radial ridges 114 may be provided along the length of handle 110.

Below handle 110 is a measuring shaft 120, formed from the same polymeric material from handle 110 in unitary molding process. The shaft 120 is a cylinder that ranges from 6 to 10 mm in length, is approximately between 0.7 mm and 1.1 mm in diameter, and has circumferential markings 121 spaced along the shaft 120 at 1 mm intervals. The markings 121 may be formed as ridges around the circumference of the shaft 120, as shown in FIG. 1, or as grooves around the circumference of shaft 120. The shaft 120 lies partly outside the canal during operations, and the markings 121 serve to inform the practitioner of the depth to which the instrument 100 has penetrated a canal.

Below the shaft 120 is a tapered shank 130 that is formed from the same polymeric material as the handle 110 and shaft 120. The shank 130 is conical, and is designed to fit inside the canal of a tooth all the way to the apical third of the canal. As such, the shank 120 ideally has a length of approximately 15-17 mm from proximal end 131 to distal end 132, and tapers from a diameter of between 0.25 and 1.0 mm at proximal end 131-which is attached to and collinear with shaft 110 to a distal end 122, the distal end 132 being sufficiently narrow to be inserted into the apical third of a canal. Typically, the distal end of the shank, without consideration of raised projections 140, will be no more than between 0.10 and 0.30 mm in diameter.

Figure 2:
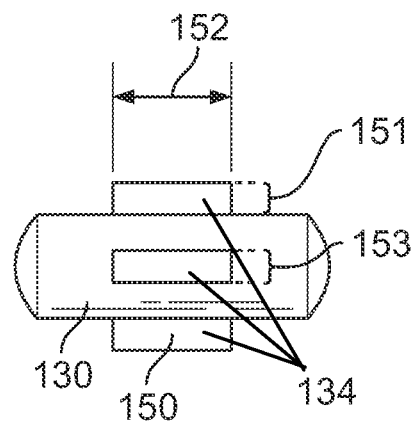
FIG. 2 is a detail view of a surface of an embodiment of the instrument according to the present invention.

A plurality of raised projections 140 are along shank 130. These raised projections 140 perform the work of cleaning the smear layer from the canal walls during use. The raised projections 140 are formed from the same polymeric material as the shank 130, and are formed with the rest of the instrument in a one-piece molding operation. The raised projections 140 extend radially from the surface of shank 130, and are made of the same stiff polymeric material as the remainder of the instrument 100 to provide sufficient mechanical action to remove the smear layer from the canal walls. The placement of raised projections 140 is denser on the apical portion 133 of the shank 130, because it is the apical third of the canal that present the most cleaning problems when treating the canal with a file and bleach solutions As shown in FIG. 2, the raised projections 140 in this embodiment may be rectangular box-shaped fins 150 that have a height 151 defined from the surface of shank 130 to top 154, typically between 0.15 and 0.4 mm. These fins 150 have a length 152 and width 153. The length 152 and width 153 of the box-shaped fins 150 may be tapered at a slight draft angle along height 151; further, the fins may and may have radius edge breaks along top 154. These features assist in fabricating the instrument by injection molding. The fins 150 may be disposed on shank 130 such that the length 152 is aligned with axis 101. In this case, the fins 150 may be arranged in a circumferential band 134 around shank 130, with a band consisting of 4-6 parallel fins 150.

Figure 3:
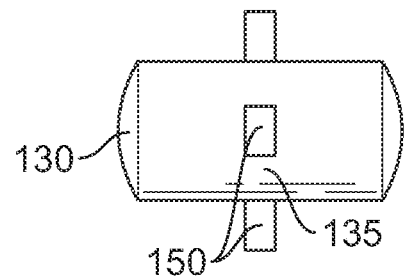
FIG. 3 is second detail view of a surface of an embodiment of the instrument according to the present invention.

Alternatively, as shown in FIG. 3, the fins 150 may be arranged with the lengths 152 oriented transverse to the axis. The fins may be arranged in a band 135 consisting of 4-6 fins that circle a circumference of shank 130.

In the embodiment of FIG. 1, bands 134 consisting of axially oriented fins 150 and bands 135 consisting of transverse-oriented fins are alternated along the shank 130, approximately 1 mm apart. This alternating orientation of fins has the advantage that multidirectional cleaning can be provided by moving the instrument 100 up and down inside the canal along the direction of axis 101, and rotating the instrument 100 around axis 101 inside the canal.

Figure 4:
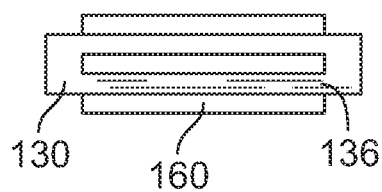
FIG. 4 is a third detail view of a surface of an embodiment of the instrument according to the present invention.
Figure 5:
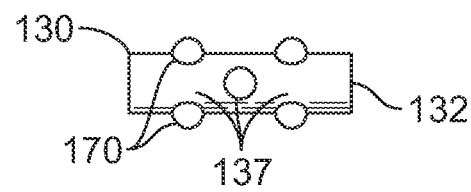
FIG. 5 is a fourth detail view of a surface of an embodiment of the instrument according to the present invention.

This pattern of alternating bands of fins 150 holds from the proximal end 131 down to the apical region 133, which begins approximately 5-6 mm from the distal end 132. In the apical region, certain projections 140 are long fins 160 (see FIG. 4) placed in two bands 136, approximately 2 and 4 mm from the distal end. These fins are disposed parallel to the axis, and are longer than the fins disposed further away from the distal end, and are approximately 1 mm in length. These longer fins provide a wide swath of cleaning at the apical third of the canal. Closest to the distal end 132, finally, the raised projections 140 are round, raised bumps 170 arising from the surface of the shank 130. These raised bumps 170 are arranged in three circumferential bands 137 of bumps 170, approximately, 0.3 mm, 0.6 mm, and 0.9 mm from the distal end. The bumps give the distal end of the shank a total width between 0.12 and 0.18 mm. The denser arrangement of projections at the apical third portion of the shank is designed to provide intense scrubbing at the apical third, which is where most of the infection problems requiring retreatment develop, even where there is only a small space for projections.

The height of raised projections 140 on shank 130 are designed to provide the right size for particular endodontic treatments. The width of the proximal end 131, including the height of projections 140 at the proximal end 131, ranges from 0.75 to 1.50 mm. The width of the distal end 132, including the height of the raised bumps 170, may range from 0.15 to 0.5 mm in diameter.

In these range listed above, it is contemplated that there would be two preferred sizes, one corresponding to a 35/.06 endodontic file, and another corresponding to a 25/.04 file (where the first of these numbers refers to the working tip diameter in 0.01 mm, and the second refers to degree of taper). In the first embodiment, the shank 130 without raised projections tapers from 0.74 mm to 0.20 mm over 16 mm, and the shank 130 with raised projections 140 tapers from 1.30 mm at proximal end 131 to 0.35 mm at distal end 132 over a length of 16 mm. In the second embodiment, the shank 130 without raised projections tapers from 0.50 mm to 0.15 mm over 16 mm, and the shank 130 with raised projections 140 tapers from 0.90 mm at proximal end 131 to 0.25 mm at distal end 132 over a length of 16 mm.

A recent study was recently concluded showing the effectiveness of the instrument of the present invention (Instrument A) with two commercially available brushes (Brush B and Brush C) directed to the same purpose. Brush B is a commercially available brush that uses very small, soft bristles. Brush C is a brush that uses very flexible, unidirectional bristles. The study demonstrates the effectiveness of the instrument of the present invention at removing microorganisms from the tooth canal.

Model Preparation:

Seventy-five single canal roots canals of recently extracted human teeth were stored in a 0.5% NaOCl solution. The teeth were decoronated perpendicular to the long axis of the root. Samples were then standardized to a uniform length of 11 mm.

The canals of each root were instrumented to a length of 11 mm using an Endosequence Rotary files 0.04 taper starting from #25 up to #40. Roots were then placed in 2.5% NaOCl for 5 minutes. The roots were then rinsed with distilled water for 10 minutes. Root preparation and infecting the dentinal tubules is based on the model of infection by Haapasalo and Ørstravik (14).

All the root samples were mounted in a 30-gauge blue needle. The models were prepared by removing the needle from the central plastic hub and hollowed out to accommodate the root segment. The root segment was secured to the needle cap encasement with Kneadatite epoxy putty (certified at 300 F and 2000 psi) (Polymetric Systems, Inc., Phoenixville, Pa.). The putty was also applied to the external root surface and apical ends of the roots creating a seal. The putty was allowed to set for 24 hours. 500 ul of Phosphate Buffered Saline Gelatin (PBSG) was pipetted into the apical cap. The completed model that consists of a cervical cap, needle encasement with the root segment and an apical cap (see FIG. 1) was then sterilized at 120 C at 15 psi for 15 mins with slow exhaust. Due to evaporation during the autoclaving process 50 ul of PBSG was lost, thus leaving 450 ul of PBSG in each model.

The study included five test groups:

Group 1 (5 teeth, Negative Control): Not infected, No use of brush or instrument;

Group 2 (5 teeth, Positive Control): Infected, Irrigation with 3 ml of PBSG, No use of brush or instrument;

Group 3 (20 teeth, Instrument A): Infected, Irrigate with 1 ml of PBSG and 10 strokes followed by irrigation with 1 ml of PBSG and 10 strokes followed by final irrigation with 1 ml PBSG;

Group 4 (20 teeth, Brush B): Infected, Irrigate with 1 ml of PBSG and 10 strokes followed by irrigation with 1 ml of PBSG and 10 strokes followed by final irrigation with 1 ml PBSG; and Group 5 (20 teeth, Brush C): infected, Irrigate with 1 ml of PBSG and 10 strokes followed by irrigation with 1 ml of PBSG and 10 strokes followed by final irrigation with 1 ml PBSG.

Cell Growth Conditions:

*E. faecalis* (ATCC 29212) was grown in 10 ml of Brain Heart Infusion (BHI) broth (Difco Laboratories, Sparks, Md.), for 24 hours in a warm room incubator at 37° C. This bacterial suspension was then used to infect the specimens.

Twelve microliters of *E. faecalis* suspension were used to inoculate the canal space of each model in groups 2-5, using a micropipette under aseptic conditions. The cervical cap of the model was removed and the bacteria were inoculated through the cervical orifice of the root segment. Samples were placed in a sealed moist container and infection of the dentin took place over a seven-day incubation period in a warm room incubator (37° C.).

Each day 12 µl of BHI broth were added aseptically to the canals during the incubation period to prevent desiccation of the roots and to provide nutrients for the microorganisms.

Treatment of Canals:

Twenty-one of the following instruments: Instrument A (according to the present invention), Brush B, Brush C and twenty-one #2, 3, 4 Gates Glidden drills were individually wrapped and autoclaved.

Group 1 (Negative Controls): Specimens were not infected. The specimens were not treated by any of the instruments or brushes.

Group 2 (Positive Controls): Specimens were infected as described above. Each specimen was dried using sterile paper points to remove any BHI broth remaining in the canal. Specimens were then irrigated using 3 ml of PBSG delivered using a 27 gauge beveled luer-lock needle via a 3 ml syringe delivered over a period of one minute. During the irrigation process irrigant was evacuated using a surgical suction tip on the high-speed evacuation suction line. After irrigation, any remaining liquid was removed using sterile paper points.

Group 3 (Instrument A): Specimens were infected as described above and dried prior to irrigation as was done in Group 2. Specimens were then irrigated using 1 ml PBSG delivered using a 27 gauge beveled leur-lock needle (BD needles) via a 3 ml syringe. During the irrigation process irrigant was evacuated using a surgical suction tip on the high-speed evacuation suction line. Instrument A was then used in 10 hand strokes in push-pull combined with half turn strokes circumferentially along the canal walls. The tooth was irrigated again with 1 ml of PBSG as described above and the 10 hand strokes repeated followed with a final rinse with 1 ml PBSG. The remaining liquid was removed using sterile paper points. The instruments were discarded after a single use and for every new specimen a new sterile instrument was used.

Group 4 (Brush B): Specimens were infected, dried and treated as in Group 3 but using the Canal brush.

Group 5 (Brush C): Specimens were infected, dried and treated as in Group 3 but using the Nano brush.

*E. faecalis* Recovery from Specimens:

For all groups the lumen was dried prior to harvesting of the dentin. Specimens were uncapped and sterile Gates Glidden burs size #2, #3 and #4 were used in sequential order to drill through the lumen of each specimen. Dentinal shavings and any material harvested from the dentin were collected into the PBSG reservoir in the apical cap. Fifty µl of PBSG was then used to wash down the dentin shavings and to make a total quantity of 500 µl of infected, undiluted sample in the apical cap. The bacterial titer in the buffer in the lower chamber was determined by serial dilutions and plating onto selective media (Thallium Acetate Agar).

Quantification of *E. faecalis*:

Thallium Acetate (TA) Agar plates were prepared using the following ingredients:

2 g thallous acetate
10 g D-glucose
10 g yeast extract
10 g proteose peptone
13 g agar
1000 ml distilled water
10 ml 10% solution triphenyl tetrazolium chloride (filtration sterilized)

Three serial dilutions were made for each specimen to quantify colony-forming units (CFUs) of *E. faecalis* on TA agar plates. Fifty microliter aliquots from each diluted samples were plated on TA agar plates. All plates were incubated overnight at 37° C. *E. faecalis* colonies appear as reddish-purple colonies on TA agar plates. Each red-purple colony was counted under magnification as an *E. faecalis* CFU.

Results

Our positive control that was infected canals rinsed with 3 ml PBSG without the use of instruments or brushes, showed an average of $1.84 \times 10^6$ cfu/ml. The groups in which the instruments or brushes were used all showed a reduction in cfu/ml (Table. 1).

When examining the reduction of cfu/ml, Instrument A of the present invention reduced the cfu's the most at $1.81 \times 10^5$ cfu/ml followed by Brush C at 2.46×105 cfu/ml. The least reduction of cfu was seen with Brush B at 6.52×105 cfu/ml.

| Groups | Mean cfu/ml | % Reduction of cfu's |
|---|---|---|
| Group 1 (Negative Control) 5 samples | 0 | — |
| Group 2 (Positive Control) 5 samples | $1.84 \times 10^6 \pm 2.3 \times 10^6$ | — |
| Group 3 (Instrument A) 20 samples | $1.81 \times 10^5 \pm 1.03 \times 10^5$ | 90.2% (most reduction) |
| Group 4 (Brush B) 20 samples | $6.52 \times 10^5 \pm 4.49 \times 10^5$ | 64% (least reduction) |
| Group 5 (Brush C) 20 samples | $2.46 \times 10^5 \pm 3.28 \times 10^5$ | 87% (second reduction) |

Statistical analysis was performed using the Bonferroni method. The tests show that there were statistically significant differences between Instrument A (Group 3) and the Positive Control (Group 2) ($p<0.001$).

While a detailed description of the preferred embodiment of the invention has been given, it should be appreciated that many variations can be made thereto without departing from the scope of the invention as set forth in the appended claims.

What is claimed is:

1. An instrument for cleaning a canal of a tooth after debriding of the canal with a file, comprising:
   a handle;
   a shank collinear with the handle comprising:
   a surface;
   a proximal end;
   a distal end;
   an upper region contiguous with the proximal end;
   an apical region contiguous with the upper region and the distal end;
   a length; and
   a longitudinal axis along the length;
   wherein the shank tapers over the length from the proximal end to a tip at the distal end, and wherein the apical region is sized and shaped to reach an apical third of the canal;
   at least one first fin located on the upper region having a length with respect to the longitudinal axis and a width, the length being longer than the width and the length of the fin being oriented parallel to the longitudinal axis; and
   at least one second fin located on the upper region having a length and a width the length being longer than the width and the length of the fin being oriented transverse to the longitudinal axis; and
   a plurality of raised bumps located on the apical region wherein the handle, shank, the plurality of raised bumps, the at least one first fin, and the at least one second fin consist of a one piece polymeric composition.

2. The instrument of claim 1, further comprising a shaft collinear with the shank, and disposed between the handle and shank, said shaft having a series of markings indicating ae depth to which the instrument has been inserted in the canal, wherein the shaft comprises an additional portion of the one piece polymeric composition.

3. The instrument of claim 1, wherein the at least one first fin and the at least one second fin are vertically spaced along the upper region at a first distance, wherein the raised bumps are vertically spaced along the apical region at a second distance, and wherein the first distance is greater than the second distance.

4. The instrument of claim 1, wherein the one piece polymeric composition is of polymeric material sufficiently stiff so as to penetrate the canal and mechanically scrub and scrape canal surfaces.

5. The instrument of claim 1, wherein the one piece polymeric composition is of polymeric material having a flexural modulus between 2500 and 3500 MPa.

6. The instrument of claim 1, wherein the one piece polymeric composition is of medium density acetal polymeric material.

7. The instrument of claim 1, wherein the tip is of a working diameter of approximately 0.35 mm and a degree of taper of approximately 0.06.

8. The instrument of claim 1, wherein the tip is of a working diameter of approximately 0.25 mm and a degree of taper of approximately 0.04.

9. The instrument of claim 1, wherein the shank is sized and shaped to be driven into the canal, and to negotiate the curvature of the canal.

10. The instrument of claim 1, wherein the apical region has a length between 5 and 6 mm.

11. The instrument of claim 1, further comprising a plurality of long fins located on the apical region, each long fin having a height measured from the surface of the shank, a width, and a length oriented parallel to the longitudinal axis of the shank and longer than the width.

12. The instrument of claim 11, wherein the length of the at least one first fin and the at least one second fin is less than the length of each of the long fins.

13. An instrument for cleaning a canal of a tooth after debriding of the canal with a file, comprising:
   a handle;
   a shank collinear with the handle comprising:
   a proximal end;
   a distal end;
   a length; and
   a longitudinal axis along the length;
   wherein the shank tapers over the length from the proximal end to a tip at the distal end, and wherein the distal end is sized and shaped to reach an apical third of the canal;
   at least one first fin having a length with respect to the longitudinal axis and a width, the length being longer than the width and the length of the fin being oriented parallel to the longitudinal axis; and
   at least one second fin having a length and a width, the length being longer than the width and the length of the fin being oriented transverse to the longitudinal axis;
   wherein the handle, shank, at least one first fin, and at least one second fin consist of a one piece polymeric composition.

14. The instrument of claim 13, further comprising a shaft collinear with the shank, and disposed between the handle and shank, said shaft having a series of markings indicating a depth to which the instrument has been inserted in the canal, wherein the shaft comprises an additional portion of the one piece polymeric composition.

15. The instrument of claim 13, wherein the one piece polymeric composition is of polymeric material sufficiently stiff as to penetrate the canal and mechanically scrub and scrape canal surfaces.

16. The instrument of claim 13, wherein the one piece polymeric composition is of polymeric material having a flexural modulus between 2500 and 3500 MPa.

17. The instrument of claim 13, wherein the one piece polymeric composition is of medium density acetal polymeric material.

18. The instrument of claim 13, wherein the tip at the distal end of the shank has a working diameter of approximately 0.35 mm and a degree of taper of approximately 0.06.

19. The instrument of claim 13, wherein the tip at the distal end of the shank has a working diameter of approximately 0.25 mm and a degree of taper of approximately 0.04.

\* \* \* \* \*